(12) United States Patent
Daussmann et al.

(10) Patent No.: US 7,943,356 B2
(45) Date of Patent: May 17, 2011

(54) ALCOHOL DEHYDROGENASE FOR THE STEREOSELECTIVE PRODUCTION OF HYDROXY COMPOUNDS

(75) Inventors: Thomas Daussmann, Singapore (SG); Hans-Georg Hennemann, Bedburg (DE)

(73) Assignee: Codexis, Inc., Redwood City, CA (US)

( * ) Notice: Subject to any disclaimer, the term of this patent is extended or adjusted under 35 U.S.C. 154(b) by 162 days.

(21) Appl. No.: 11/629,000

(22) PCT Filed: Jun. 4, 2005

(86) PCT No.: PCT/EP2005/006034
§ 371 (c)(1),
(2), (4) Date: Nov. 24, 2008

(87) PCT Pub. No.: WO2005/121326
PCT Pub. Date: Dec. 22, 2005

(65) Prior Publication Data
US 2009/0162893 A1    Jun. 25, 2009

(30) Foreign Application Priority Data
Jun. 11, 2004 (DE) .......................... 10 2004 029 112

(51) Int. Cl.
C12N 9/04 (2006.01)
C12P 7/02 (2006.01)
C12P 21/04 (2006.01)
C12Q 1/00 (2006.01)
C12Q 1/32 (2006.01)
C07H 21/04 (2006.01)

(52) U.S. Cl. .............. 435/190; 435/155; 435/4; 435/26; 435/69.1; 435/71.1; 536/23.2

(58) Field of Classification Search .................. None
See application file for complete search history.

(56) References Cited

U.S. PATENT DOCUMENTS
5,908,924 A    6/1999  Burdette et al.

FOREIGN PATENT DOCUMENTS
DE       4209022 A1    10/1993
WO    WO-9732012 A1     9/1997
WO    WO-03091423 A1   11/2003

OTHER PUBLICATIONS

Branden et al. Introduction to Protein Structure, Garland Publishing Inc., New York, p. 247, 1991.*
"International Search Report for Application No. PCT/EP2005/006034", 3 Pages.
Bao, Q., et al., "A complete sequence of the *T. tengcongensis* genome", *Genome Res.*, 12(5), (2002), 689-700.
Bao, Q., et al., "Threonine dehydrogenase and related Zn-dependent dehydrogenases.", *EMBL Database*, Database accession No. Q8RBWS, (2004).
Burdette, Douglas S., et al., "Cloning and expression of the gene encoding the *Thermoanaerobacter ethanolicus* 39E secondary-alcohol dehydrogenase and biochemical characterization of the enzyme.", *Biochemical Journal*, vol. 316, No. 1, (1996), 115-122.
Burstein, Y., "Nucleotide sequence of the *Thermoanaerobium brockii* gene encoding alcohol", *Database EMBL-SVA*, Database Accession No. X64841, (1997).
Eckstein, M., et al., "Recent developments in NAD(P)H regeneration for enzymatic reductions in one- and two-phase system", *Biocatalysis and Biotransformation*, vol. 22, No. 2, (2004), 89-96.

* cited by examiner

*Primary Examiner* — Yong D Pak (57) ABSTRACT

The invention relates to a DNA sequence encoding an NADP-dependent alcohol dehydrogenase, to a vector containing at least one copy of the DNA sequence and to prokaryotic or eukaryotic host cells that are transformed or transfected with the DNA sequence. The invention also relates to the NADP-dependent alcohol dehydrogenase, to a method for the production and the use of the alcohol dehydrogenase and to a method for the stereoselective production of secondary alcohols.

7 Claims, 3 Drawing Sheets

Figure 1

```
ATGAAAGGTTTTGCAATGCTCAGTATCGGTAAGGTTGGCTGGATTGAGGTAGAAAAGCCT
AATCCAGGACCCTTTGATGCTATCGTAAGACCCCTAGCTGTGGCCCCTTGCTCTTCGGAC
ATTCACACTGTTTTTGAAGGAGGCCTTGGTGAACTTCACAACGCAGTGCTAGGTCACGAA
GCTGTAGGTGAAGTAGTCGAAGTCGGTAGTGAAGTAAAAGACTTTAAACCTGGTGATAAG
GTGGTCATTCCTGCTATCACTCCTGATTGGAGAACGTTAGATGTTCAACGTGGTTATCAT
CAGCAGTCCGGAGGTATGCTTGCTGGTTACAAGTTCACAGCCCAGAAACCTGGTGTGTTC
GCCGAGTACATCTACGTTAACGATGCAGACATGAATCTTGCTCATTTACCTGACGGCATC
TCTTTAGAAGCGGCCGTCATGATCACAGATATGATGACTACCGGTTTTCACGGAGCCGAA
CTGGCAGAAATAGAATTAGGTGCAACAGTAGCGGTTTTGGGTATTGGTCCAGTAGGTCTT
ATGGCAGTCGCTGGTGCCAAATTGCGGGGTGCTGGAAGAATTATTGCAGTAGGCAGTAGA
CCTGTTTGTGTAGATGCTGCAAAATACTATGGAGCTACTGATATTGTAAACTATAAAAAT
GGTCCTATCGACAGTCAGATTATGGATTTAACGAAAGGCAAAGGTGTTGATGCTGCCATC
ATCGCTGGAGGAAATGTTGACATCATGGCTACAGCAGTTAAGATTGTTAAACCTGGTGGC
ACCATTGCTAATGTAAATTACTTTGGCGAAGGAGATGTTTTGCCTGTTCCTCGTCTTGAA
TGGGGTTGCGGCATGGCTCATAAAGCTATAAAAGGCGGTTTATGCCCTGGTGGACGTCTA
AGAATGGAAAGACTGATTGACCTTGTTTTTTATAAGCGTGTCGATCCTTCCAAACTCGTC
ACTCATGTTTTTCAAGGATTTGATAATATTGAAAAAGCTCTAATGCTGATGAAAGATAAA
CCAAAGGACCTAATCAAACCTGTTGTAATATTAGCATAA
```

FIGURE 2

Met Lys Gly Phe Ala Met Leu Ser Ile Gly Lys Val Gly Trp Ile Glu Val Glu Lys Pro Asn Pro Gly
Pro Phe Asp Ala Ile Val Arg Pro Leu Ala Val Ala Pro Cys Ser Ser Asp Ile His Thr Val Phe Glu Gly
Gly Leu Gly Glu Leu His Asn Ala Val Leu Gly His Glu Ala Val Gly Glu Val Val Glu Val Gly Ser
Glu Val Lys Asp Phe Lys Pro Gly Asp Lys Val Val Ile Pro Ala Ile Thr Pro Asp Trp Arg Thr Leu
Asp Val Gln Arg Gly Tyr His Gln Gln Ser Gly Gly Met Leu Ala Gly Tyr Lys Phe Thr Ala Gln Lys
Pro Gly Val Phe Ala Glu Tyr Ile Tyr Val Asn Asp Ala Asp Met Asn Leu Ala His Leu Pro Asp Gly
Ile Ser Leu Glu Ala Ala Val Met Ile Thr Asp Met Met Thr Thr Gly Phe His Gly Ala Glu Leu Ala
Glu Ile Glu Leu Gly Ala Thr Val Ala Val Leu Gly Ile Gly Pro Val Gly Leu Met Ala Val Ala Gly Ala
Lys Leu Arg Gly Ala Gly Arg Ile Ile Ala Val Gly Ser Arg Pro Val Cys Val Asp Ala Ala Lys Tyr Tyr
Gly Ala Thr Asp Ile Val Asn Tyr Lys Asn Gly Pro Ile Asp Ser Gln Ile Met Asp Leu Thr Lys Gly
Lys Gly Val Asp Ala Ala Ile Ile Ala Gly Gly Asn Val Asp Ile Met Ala Thr Ala Val Lys Ile Val Lys
Pro Gly Gly Thr Ile Ala Asn Val Asn Tyr Phe Gly Glu Gly Asp Val Leu Pro Val Pro Arg Leu Glu
Trp Gly Cys Gly Met Ala His Lys Ala Ile Lys Gly Gly Leu Cys Pro Gly Gly Arg Leu Arg Met Glu
Arg Leu Ile Asp Leu Val Phe Tyr Lys Arg Val Asp Pro Ser Lys Leu Val Thr His Val Phe Gln Gly
Phe Asp Asn Ile Glu Lys Ala Leu Met Leu Met Lys Asp Lys Pro Lys Asp Leu Ile Lys Pro Val Val
Ile Leu Ala

FIGURE 3

ALCOHOL DEHYDROGENASE FOR THE STEREOSELECTIVE PRODUCTION OF HYDROXY COMPOUNDS

RELATED APPLICATIONS

This application is a nationalization under 35 U.S.C. 371 of PCT/EP2005/006034, filed Jun. 4, 2005, and published as WO 2005/121326 A2 on Dec. 22, 2005, which claimed priority under U.S.C. 119 to German Application No. 10 2004 029 112.8, filed Jun. 11, 2004, which applications and publication are incorporated herein by reference and made a part hereof.

The present invention relates to a DNA molecule which codes for a NADP-dependent alcohol dehydrogenase, a vector which contains at least one copy of the DNA sequence, and prokaryotic or eukaryotic host cells which are transformed or transfected with the DNA sequence. The invention also relates to the NADP-dependent alcohol dehydrogenase, a process for the production and the use of the alcohol dehydrogenase and a process for the stereoselective production of secondary alcohols.

Alcohol dehydrogenases are a well-known class of enzymes, with which keto compounds can be enzymatically reduced to alcohols.

The preparation of optically active compounds, e.g. of alcohols and amines by biocatalytic means is becoming increasingly important. As a route for the large-scale industrial synthesis of these compounds, the coupled use of two dehydrogenases with cofactor regeneration is known from DE 19753350 A1.

The in situ regeneration of NADPH with an NADP-dependent glucose dehydrogenase, glucose-6-phosphate dehydrogenase or other NADP-dependent oxidoreductases is a possibility here (see Y. Yasohara, N. Kizaki, J. Hasegawa, M. Wada, M. Kataoka and S. Shimizu, Tetrahedron: Asymmetry 2001, 12, 1713-1718).

Alcohol dehydrogenases (ADHs) are of interest in this connection, and actually in a balanced coupled enzymatic system enable inter alia the production of enantiomerically enriched alcohols starting from ketones by enantioselective reduction, or from racemic alcohols by kinetic racemate splitting (DE 10037101; as an up-to-date, comprehensive overview on the state of the technology, see: W. Hummel, Adv. Biochem. Engineering/Biotechnology 1997, 58, 145-184).

Substrate-coupled cofactor regeneration, which manages without a second dehydrogenase, is also much used. Here the cofactor is regenerated in a reverse synthesis direction by the alcohol dehydrogenase necessary for the desired conversion, with the use of a secondary substrate added in excess (any alcohol such as for example isopropanol or ethanol) (see W. Stampfer, B. Kosjek, C. Moitzi, W. Kroutil and K. Faber, Angew. Chem. Int. Ed. Engl. 2002 Mar. 15; 41(6): 1014-7). ADHs are classified under the Class E.C.1.1.1.1 or E.C.1.1.1.2 and thus come under the so-called oxidoreductases. They occur in a number of organisms (Enzyme Catalysis in Organic Synthesis, ed.: K. Drauz and H. Waldmann, 1995, VCH, vol. II, 595ff).

"Broad band enzymes" which stereoselectively convert a broad spectrum of substrates are of interest.

Commercially available for preparative use on the laboratory scale are for example the ADH from yeast (YADH), from horse liver (HLADH) and from *Thermoanaerobacter brockii* or *Thermoanaerobium brockii*, which are used for the preparation of alcohols. Apart from these, there are a number of other ADHs available for purchase, which however, as indeed the name shows, convert specific substrates, such as for example a number of steroid dehydrogenases, which preferably convert alcohol groups in steroid structures or glycerol dehydrogenases, which convert glycerine or finally also sugar-converting enzymes such as the glucose dehydrogenase already mentioned.

Most of the ADHs hitherto known in the literature are "S-specific" (where for formal reasons of nomenclature the designation S and R can also sometimes reverse). On the other hand the ADHs from the *Lactobacillus* strains are said to be R-specific (see C. W. Bradshaw, W. Hummel, C.-H. Wong, J. Org. Chem. 1992, 57, 1532), and also another from *Pseudomonas* known from the literature (P. Hildebrandt, T. Riermeier, J. Altenbuchner, U. T. Bornscheuer, Tetrahedron: Asymmetry 2001, 12, 1207), which was recently described by the Altenbuchner and Bornscheuer team. The working group around Keinan and Lamed in addition reported an ADH from *Thermoanaerobium brockii* (E. Keinan, E. K. Hafeli, K. K. Seth, R. Lamed, J. Am. Chem. Soc. 1986, 108, 162) which displays an (R) specificity for small substrates, but in contrast is (S) specific for larger substrates.

The ADH T described in this invention is (S) selective. A number of members of the (S) specific alcohol dehydrogenases are admittedly already known, however their industrial applicability is mostly very limited. This is borne out not least by the very few industrial use processes with such enzymes in contrast to the large number of known ADHs. The (S) ADH from yeast is admittedly a valuable NADH-dependent enzyme, but preferentially converts primary alcohols so that it is of little significance for the production of chiral alcohols.

The NADH-dependent (S) ADH from horse liver (HLADH) is without doubt to date the most frequently used alcohol dehydrogenase in the academic field, as is clearly shown by the large number of publications with this enzyme (see e.g. overview in: K. Faber, Biotransformations in Organic Chemistry, 4$^{th}$ Edition, Springer-Verlag, 2000, 184f). Unfortunately owing to the lack of availability, this enzyme is not really an option for industrial use. (S) ADH from horse liver is very expensive (ca. 0.5 euro per unit), since it is not so far available recombinantly.

Also, the substrate spectrum preferentially comprises cyclic ketones, and it does not convert ketones with aromatic side-chains (of the acetophenone type). From the industrial point of view, however, it is precisely this aromatic ketone substance class which is of great importance owing to the large number of applications for these as key intermediates in the pharmaceutical field (for selected examples, see: a) R. A. Holt, S. R. Rigby (Zeneca Limited), U.S. Pat. No. 5,580,764, 1996; b) T. J. Blacklock, P. Sohar, J. W. Butcher, T. Lamanec, E. J. J. Grabowski, J. Org. Chem. 1993, 58, 1672-1679; c) R. A. Holt, Chimica Oggi, Chemistry Today 1996, 9, 17-20; d) F. Bracher, T. Litz, Arch. Pharm. 1994, 327, 591-593; e) S. Y. Sit, R. A. Parker, I. Motoc, W. Han, N. Balasubramanian, J. Med. Chem. 1990, 33, 2982-2999; and f) A. Zaks, D. R. Dodds, Drug Discovery Today 1997, 2, 513-530).

The NADP-dependent ADH (TBADH) from *Thermoanaerobacter brockii* or *Thermoanaerobium brockii* is available recombinantly. The price of NADP is about 3 to 4 times higher than that of NAD. Nonetheless, with the use of a suitable regeneration system the costs of the cofactor are acceptable. However, the substrate spectrum of TBADH is confined to aliphatic ketones. For example, no ketones with aromatic side-chains (of the acetophenone type) are converted.

A further readily available (S) selective ADH is the enzyme from *Rhodococcus erythropolis* (DE 4209022.9, WO03/091423). Here a broad substrate spectrum is accepted. A disadvantage of this ADH for an industrial application is however the need for enzyme-coupled cofactor regeneration. A cheap secondary substrate such as for example isopropanol cannot be used.

In contrast, with the (S) ADH from *Rhodococcus ruber* (W. Stampfer, B. Kosjek, C. Moitzi, W. Kroutil and K. Faber, Angew. Chem. Int. Ed. Engl. 2002 Mar. 15; 41(6): 1014-7), the substrate-coupled route for cofactor regeneration can be successfully adopted. Here the essential disadvantage for an industrial conversion must be discerned in the limited availability of the enzyme; so far, the enzyme can only be prepared from the wild type, and cloning and overexpression has not so far been successful.

Obviously therefore, there is still a need for the provision of industrially interesting ADHs without the aforesaid disadvantages.

The purpose of the present invention is to describe a novel stereoselective alcohol dehydrogenase and the DNA necessary for its recombinant preparation.

Figure 1:
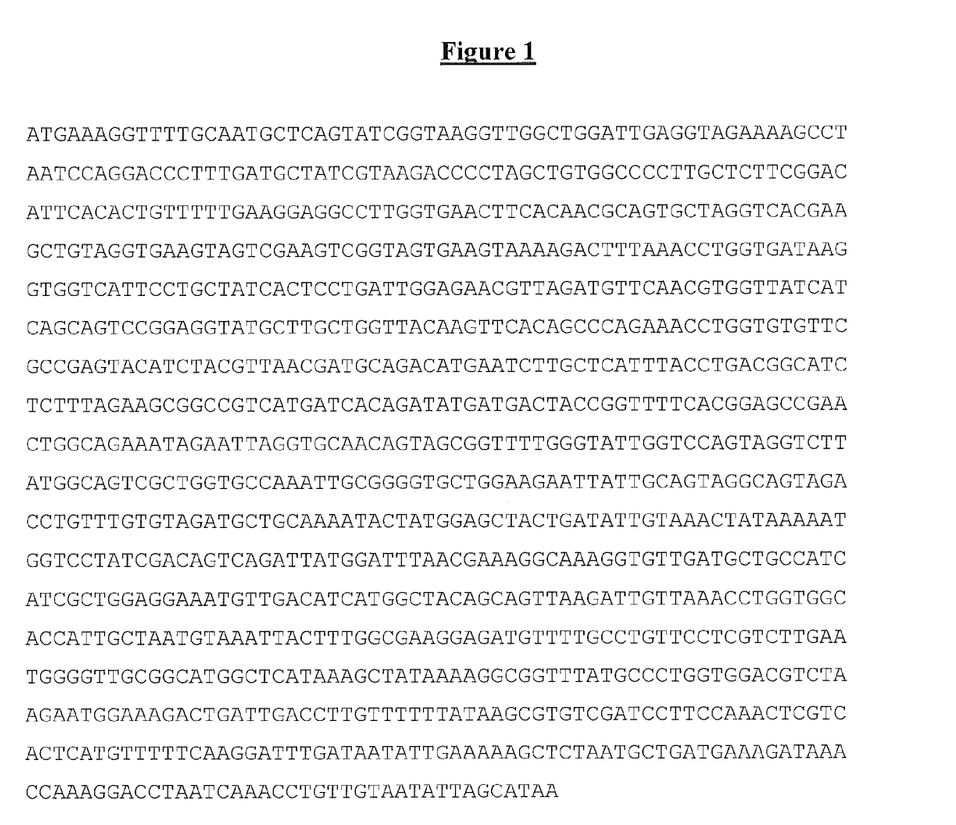
Figure 2:
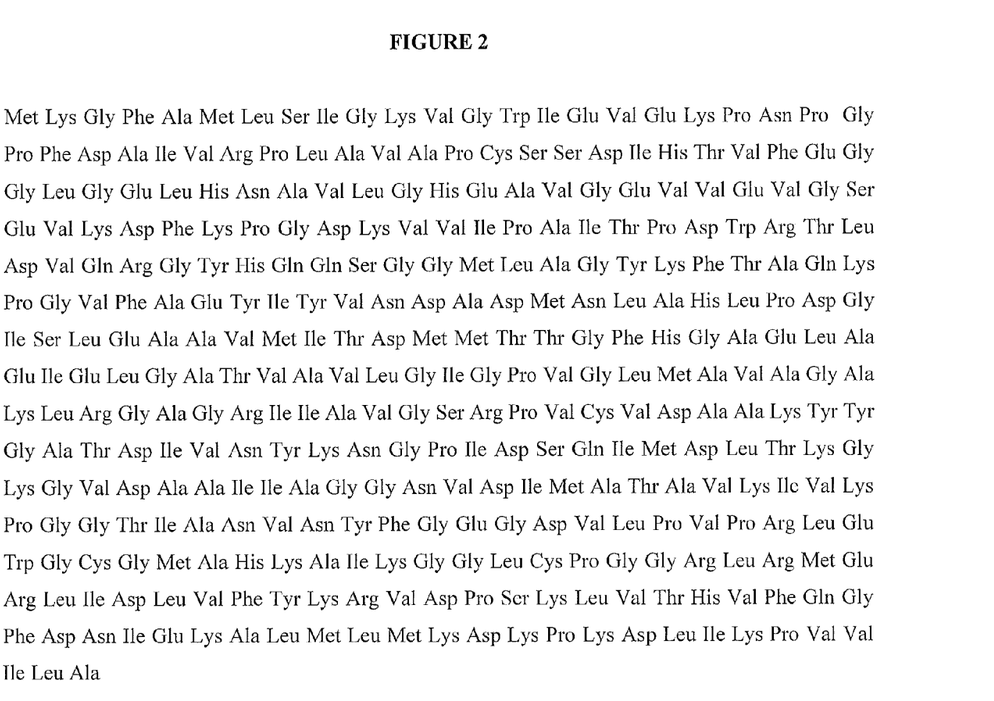

This problem is solved by means of a DNA molecule as claimed in claim 1 and an alcohol dehydrogenase as claimed in claims 5 and claim 6. Reference is also made to FIG. 1 which depicts the alcohol dehydrogenase (ADH) DNA sequence of a *Thermoanaerobacter* species (SEQ ID NO: 1) and FIG. 2 which depicts the protein sequence (SEQ ID NO: 2) encoded by the DNA sequence of FIG. 1.

The DNA according to the invention is derived from *Thermoanaerobacter* species.

Starting from the sequence, the DNA can be synthesized in known manner. Particularly suitable for this are automated solid phase methods, wherein activated monomers are successively added to a growing chain which is bound to an insoluble matrix. Reactive groups which are not to react during the synthesis are blocked by protective groups. After the complete synthesis of the DNA chain, the protective groups are cleaved off and the DNA strand detached from the matrix.

DNA molecules with a predefined sequence are also commercially available. They are produced by firms which have specialized in the production of any desired sequences. Thus it is no longer necessary to have the starting organism available in order to obtain a DNA molecule.

The term "stringent conditions" used in claim 1 describes conditions for the hydrolysis and the washing of the DNA. Stringent conditions are known to the skilled person and can be found in the literature (e.g. Current Protocols in Molecular Biology, John Wiley & Sons, N.Y., 1989, 6.3.1-6.3.6). In this literature reference, aqueous and non-aqueous processes are described. Preferred examples of stringent hybridization conditions are also described in U.S. Pat. No. 6,740,514.

The alcohol dehydrogenase according to the invention is thermally stable and is also described below as ADH T. The enzyme described (S)-selectively converts aliphatic alcohols, ketones and diketones, and also those with aromatic side-chains (of the acetophenone type).

Its thermal stability enables conversions over a wide temperature range between 30° and 70° C. By the use of a thermally stable glucose dehydrogenase, the reaction temperature can be selected almost without reference to the enzymes. Owing to the solvent tolerance of ADH T, however, substrate-coupled cofactor regeneration, e.g. through the use of isopropanol, is also possible.

Figure 3:
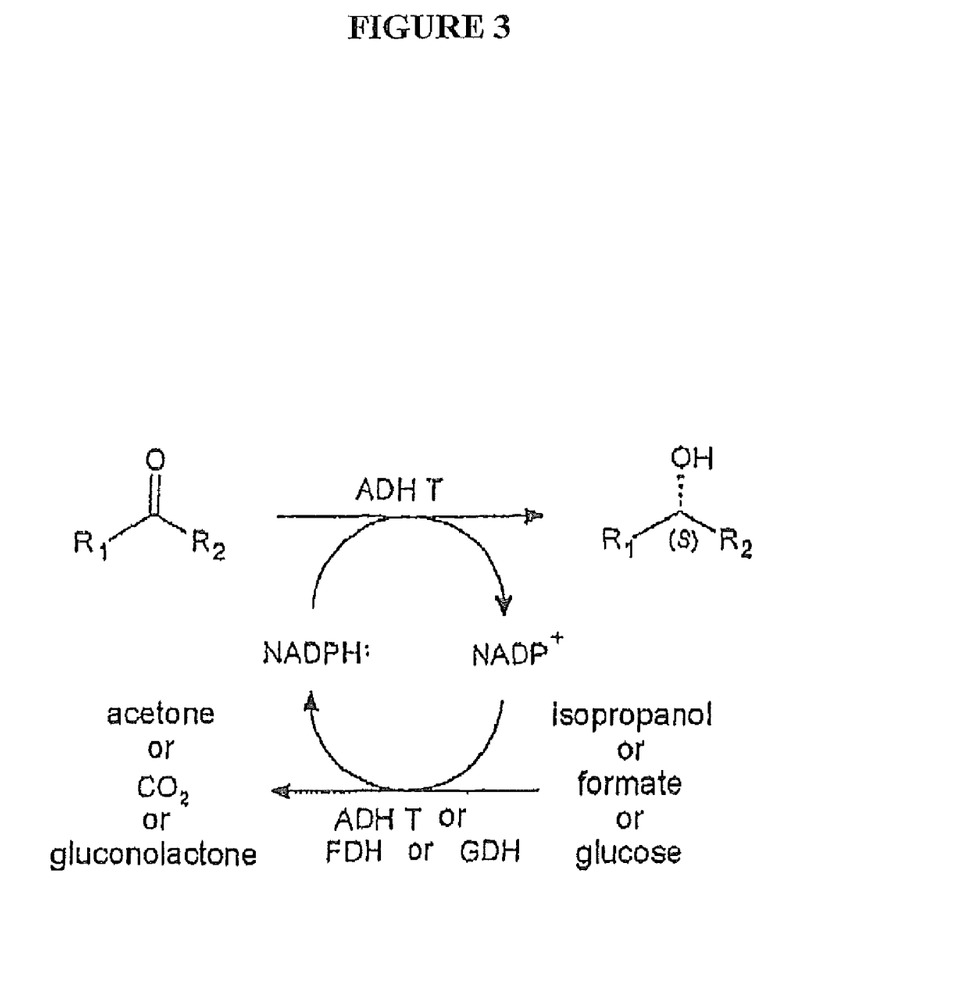

The use of alcohol dehydrogenase according to the invention is shown diagrammatically in FIG. 3 and this embodiment includes the use of cofactor generation.

From U.S. Pat. No. 5,908,924 A1, an alcohol dehydrogenase from *Thermoanaerobacter ethanolicus* 39E is known, the DNA sequence and amino acid sequence whereof display a certain homology to the DNA molecule according to the invention and the ADH T according to the invention. The DNA molecules described and claimed in said US patent are not an object of the present invention, and compared to the alcohol dehydrogenase from *Themmoanaerobacter ethanolicus* 39E the alcohol dehydrogenase ADH T displays considerably unforeseeable advantages, as will be demonstrated below by comparison examples.

The present invention also relates to a vector which contains at least one copy of the DNA sequence as claimed in claim 1 and also a prokaryotic or eukaryotic host cell which is transformed or transfected with a DNA sequence as claimed in claim 1 in a manner such that it enables the host cell to express said alcohol dehydrogenase. The host is advantageously selected from the group consisting of *Escherichia coli, Saccharomyces cerevisiae, Pichia pastoris* and *Bacillus subtilis*.

Essentially, the fermentation and expression for the production of the alcohol dehydrogenase according to the invention ADH T can be carried out under the conditions known to the skilled person, as described for example by M. I. Viitanen, A. Vasala, P. Neubauer and T. Alatossava in Microbial Cell Factories 2003, 2:2. However, this procedure results only in low activity yields of ca. 200 U/g cell wet weight. Surprisingly, it was found that the activity yield can be considerably increased if zinc ions are added to the culture medium. Thus the activity yield was increased tenfold by the addition of 1 mM zinc sulfate. The invention therefore also relates to a process for the production of the alcohol dehydrogenase according to the invention, wherein prokaryotic or eukaryotic host cells which have been transformed or transfected with a DNA sequence as claimed in claim 1 in a manner such that the host cells are enabled to express the alcohol dehydrogenase are cultured in a culture medium which contains zinc ions in a concentration of 0.1 to 5 mM and the alcohol dehydrogenase is isolated as expression product of the DNA sequence.

The dependence of the activity yield on the zinc concentration is shown in the following Table 1.

TABLE 1

Study of different zinc concentrations in high density cell fermentation with heterologous expression of ADH T in *E. coli*. Induction was performed at $OD_{600}$ 30 with 0.4 mM IPTG for 14 hours at 30° C. The activity is given per gram cell wet weight after the induction period.

| | Zinc concentration | | | | |
| --- | --- | --- | --- | --- | --- |
| | 0.0 mM | 0.5 mM | 1.0 mM | 2.0 mM | 3.0 mM |
| Activity | 200 U/g | 2900 U/g | 2000 U/g | 1113 U/g | 1118 U/g |

In spite of its thermal stability, the isolated ADH T cannot be stored for long under standard conditions (50 mM Tris-Cl, pH 7.0). The half-life is only ca. 4 days. By addition of e.g. NaCl, the half-life can be increased to more than 40 days (Table 2).

TABLE 2

Activity of the isolated ADH T under different storage conditions at 4° C.

| | NaCl concentration | | | |
| --- | --- | --- | --- | --- |
| | 0.0 M | 0.2 M | 0.5 M | 1.0 M |
| Activity Start | 105 U/ml | 105 U/ml | 105 U/ml | 105 U/ml |
| Activity Day 5 | 24 U/ml | 101 U/ml | 113 U/ml | 115 U/ml |

TABLE 2-continued

Activity of the isolated ADH T under different storage conditions at 4° C.

| | NaCl concentration | | | |
|---|---|---|---|---|
| | 0.0 M | 0.2 M | 0.5 M | 1.0 M |
| Activity Day 10 | 6 U/ml | 7 U/ml | 86 U/ml | 119 U/ml |
| Activity Day 20 | 0 U/ml | 0 U/ml | 0 U/ml | n.d. |
| Activity Day 40 | 0 U/ml | 0 U/ml | 0 U/ml | 78 U/ml | n.d. = not determined

However, the addition of zinc ions to the prepared enzyme leads rapidly to its inactivation.

Storage at −20° C. showed high stability over at least 3 months with addition of glycerine, in particular at a concentration of 50%.

Also suitable as stabilizers of the enzyme preparation in the sense of this application are glycol, polyethylene glycol and sugars such as for example trehalose or sucrose and combinations of these substances as such or in combination with a substance for suitable raising of the ionic strength.

Further characterization of the recombinant ADH T:

The pH optimum was found to be pH 7.0 (Table 3 and 4).

TABLE 3

Activity of the isolated ADH T at different pH values.

| | pH value | | | | |
|---|---|---|---|---|---|
| | 5.0 | 6.0 | 7.0 | 8.0 | 9.0 |
| Measured activity | 53 U/ml | 134 U/ml | 192 U/ml | 146 U/ml | 13 U/ml |

TABLE 4

The activity at pH values closer to pH 7.0 was studied again separately.

| | pH value | | |
|---|---|---|---|
| | 6.5 | 7.0 | 7.5 |
| Relative activity | 66% | 100% | 74% |

The thermal stability is also very good. The activity of the ADH T was still at 75% of the starting value even after 12 hrs at 50° C.

In the purified state described here, it converts aliphatic and aromatic ketones, aldehydes, 2- or 3-keto esters and diketones. Further data on the substrate spectrum is shown in Table 5.

TABLE 5

Relative activities of the purified ADH T in the reduction of different substrates (10 mM). The activity with acetone was set at 100%.

| Substrate | Relative activity |
|---|---|
| Acetone | 100% |
| 2-butanone | 72% |
| 2-pentanone | 31% |
| 2-hexanone | 30% |
| 2-octanone | 9% |
| Monochloroacetone | 71% |
| Acetaldehyde | 101% |
| 2-methylbutyraldehyde | 52% |
| Diacetyl | 154% |
| 2,4-pentanedione | 77% |
| 2,5-hexanedione | 74% |
| Ethyl acetoacetate | 22% |
| Ethyl 4-chloroacetoacetate | 45% |
| Acetophenone | 28% |
| p-chloroacetophenone | 17% |
| 2-acetylpyridine | 36% |
| 3-butyn-2-one | 76% |
| 1,2-cyclohexanedione | 5% |
| Pyruvate | 2% |
| 2-oxobutyric acid | 28% |
| 4-chloro-2-butanone | 66% |
| 4-hydroxy-2-butanone | 13% |
| 3-octanone | 26% |
| Phenacyl chloride | 25% |

The comparison of the activity of the ADH T with that of the secondary alcohol dehydrogenase from *Thermoanaerobacter ethanolicus* 39E (U.S. Pat. No. 5,908,924) with regard to the conversion of diketones is interesting (Table 6).

The corresponding diols play a major part in the synthesis of chiral ligands of chemical homogeneous catalysts and must therefore be of the highest enantiomeric and diastereomeric purity.

TABLE 6

Relative activity of the ADH T with various diketones.

| | | 2,4-pentanedione | | 2,5-hexanedione | |
|---|---|---|---|---|---|
| Enzyme | Standard substrate | rel. activity | spec. activity | rel. activity | spec. activity |
| ADH T 1.5 mg/ml | acetone (10 mM) 106 U/ml | 77% | 55.4 U/mg | 74% | 52.7 U/mg |
| ADH-TE 2.45 mg/ml | acetone (10 mM) 75 U/ml | 34% | 10.3 U/mg | 12% | 3.8 U/mg |

The reaction of 2,4-pentanedione with ADH T is suitable both for the preparation of (S)-2,4-hydroxy-2-pentanone and also of (S,S)-2,4-pentanediol.

The reaction can yield both products in very high enantiomeric and diastereomeric purity (Table 7).

TABLE 7

The substrate and product contents after 48 hrs incubation at 30° C. in 50 mM Tris/HCl pH 7.0 are shown.
For the preparation of (S)-4-hydroxy-2-pentanone, 5 U/ml of enzyme with substrate-coupled cofactor regeneration using isopropanol (10%) were used, and for the preparation of (S,S)-2,4-pentanediol, 10 U/ml were used with enzyme-coupled cofactor regeneration using glucose dehydrogenase.
In both cases the cofactor is NADP.

|  | 2,4-pentanedione (unconverted) | (R)-4-hydroxy-2-pentanone | (S)-4-hydroxy-2-pentanone | meso-2,4-pentane-diol | (S,S)-2,4-pentane-diol |
|---|---|---|---|---|---|
| ADH T substrate-coupled | — | — | 82.6% | — | 17.4% |
| ADH T enzyme-coupled | — | — | 14.6% | — | 85.4% |
| ADH TE substrate-coupled | 84.8% | — | 0.6% | 14.6% | — |
| ADH TE enzyme-coupled | — | 7.1% | 17.3% | 15.7% | 59.9% |

Here it can be seen that the ADH T not only achieves high conversion levels, but also in contrast to ADH TE has far better enantio- and diastereoselectivity for the reduction of 2,4-pentanedione.

2,5-hexanedione is also reduced to the diol by ADH T with very good values for conversion and enantio and diastereoselectivity (Table 8).

TABLE 8

The values for conversion after 48 hrs and ee/de for the (S,S) enantiomer are shown with the same quantities of enzyme used as in Table 6.

|  | 2,5-hexanedione | |
|---|---|---|
|  | Conversion to diol | ee/de |
| ADH T substrate-coupled | 10.6% | 100% |
| ADH T enzyme-coupled | 82.4% | 100% |
| ADH TE substrate-coupled | 0.3% | not determinable |
| ADH TE enzyme-coupled | 3.3% | not determinable |

The ee/de value of 100% signifies absolute enantiomeric and diastereomeric purity of the diols prepared. By means of the invention described here, the ADH T can for the first time be obtained in sufficient quantity to produce enantiomerically pure diols on the kilogram scale.

The improvement in the stability of the isolated enzyme described by the application markedly increases the product yield of chiral alcohols in a biotransformation with ADH T, based on the quantity of enzyme used.

In fact, it can be shown that the enantioselectivity in the reduction of critical ketones such as 2-pentanone or 2-butanone by substrate-coupled cofactor regeneration with isopropanol is also far better than with the use of enzyme-coupled cofactor regeneration.

Also, the achievable enantiomeric purity of the product depends on the quantity of isopropanol used (Table 9).

TABLE 9

The conversion levels and enantiomeric excesses (ee) are shown for a conversion of 200 mM of 2-pentanone with 3 U/ml of ADH T and 0.05 mM NADP in 100 mM of Tris-Cl pH 7.0 with different isopropanol concentrations for the substrate-coupled cofactor regeneration.

|  | 20% isopropanol | | 50% isopropanol | |
|---|---|---|---|---|
|  | Conversion | ee | Conversion | ee |
| 24 hours | 85.3% | 98.9% | 93.8% | 99.9% |
| 48 hours | 86.5% | 98.3% | 94.2% | 99.9% |

Activity Measurement

The activities were determined by photometric measurement of the decrease in the cofactor. Measurement batch: 50 mM Tris-Cl, pH 7.0 with 10 mM substrate and 0.2 mM NADPH. The measurement batch for ADH-TE also contained 1 mM of $MgCl_2$.

The decrease in NADPH was followed at 340 nm for one minute after addition of the enzyme. Sufficient enzyme was added for the activity to be between 0.5 and 1.5 U/ml and the measurement volume was 1 ml.

1 U corresponds to the quantity of enzyme which converts 1 μmol of substrate per minute.

Cloning of the Alcohol Dehydrogenase from *Thermoanaerobacter* Species

For the cloning of the alcohol dehydrogenase from *Thermoanaerobacter* species, it was assumed that the corresponding gene sequence of that from the related organisms *Th. ethanolicus*, *Th. brockii* and *Th. tengcongensis* is sufficiently similar to derive a primer pair from the sequences thereof.

The primer sequences derived are (SEQ ID NO: 3)
N:
CAT ATG AAA GGT TTT GCA ATG CTC AGT ATC GG
and (SEQ ID NO: 4)
C:
CTC GAG TTA TGC TAA TAT TAC AAC AGG TTT GAT TAG G.

An Nde I cleavage site was attached to the N-terminal primer, and an Xho I cleavage site to the C-terminal primer, as emphasized in bold in the sequence.

After dilution to 100 pmol/µl, the primers were phosphorylated with the T4 polynucleotide kinase from Roche.

Preparation of Genomic DNA and PCR 100 mg of freshly fermented biomass of the organism *Thermoanaerobacter* species were withdrawn. The genomic DNA was isolated with the genomic Tips from the firm QIAGEN.

The PCR reaction was performed with a program which contains an annealing gradient of 10° C. around the core temperature of 55° C.

The remaining parameters were selected as described in the Roche high fidelity protocol for fragments of ca. 1000 bp.

The subsequent gel electrophoresis showed a PCR product of the expected size of ca. 1000 bp in all 12 batches.

Cloning into pUC 18

The DNA was ligated into the Sma I-cleaved and dephosphorylated vector pUC 18 using the T4 ligase from Roche.

After transformation of the construct into DH5α *E. coli*, plasmid isolation and restriction analysis, several clones with an insert-bearing vector could be identified.

The construct was named pUC18[ADH T]. Its sequence was determined.

Cloning into pET24a

The gene for the alcohol dehydrogenase was cleaved out of the vector pUC18[ADH T] with the restriction enzymes Nde I and Xho I and ligated into the vector pET24a, digested with the same enzymes.

In preliminary experiments, dephosphorylation of this vector was found to be unnecessary.

The ligation mixture was again transformed into DH5α.

After plasmid isolation and restriction analysis, several clones with the correct insert could also be isolated here.

The construct produced was named pET24a[ADH T] and was transformed into the expression host strain Rosetta-(DE3)pLacI from the firm Novagen.

Expression Test

The strain pET24a[ADH T] in Rosetta[DE3]pLacI thus obtained was cultured in LB medium for five hours, induced with 0.5 mM IPTG and further cultured overnight.

The cells were harvested, disintegrated by ultrasound in 100 mM Tris-Cl pH 7.5 and the cell debris removed by centrifugation.

The activity of the overproduced protein with the substrate acetone was found to be 5000 U/g cell wet weight.

Sequence Analysis

The DNA sequence found was translated into an amino acid sequence by means of the program "Clone" and compared with the corresponding sequence from *Th. ethanolicus*.

High Cell Density Fermentation of *E. Coli*

Mineral Salt Medium:
4.0 g/l $NaH_2PO_4 \times 2H_2O$
14.6 g/l $K_2HPO_4$
0.5 g/l $NH_4Cl$
2.5 g/l $(NH_4)_2SO_4$
1.0 g/l $(NH_4)_2H$ citrate
2.0 g/l $Na_2SO_4$ The medium was heat-sterilized and 2 ml/L each of 1 M $MgSO_4$ and trace element solution consisting of
0.74 g/l $CaCl_2 \times 6H_2O$
0.18 g/l $ZnSO_4 \times 7H_2O$
0.1 g/l $MnSO_4 \times H_2O$
20.1 g/l $Na_2$ EDTA
16.7 g/l $FeCl_3 \times 6H_2O$
0.1 g/l $CuSO_4$
0.104 g/l $CoCl_2$
and 34 mg/l of thiamine were added. 20 g/l glucose was used as the carbon source.

For the fermentation of a bacterium rendered capable of overproduction of ADH T, in this case *E. coli*, $ZnSO_4$ was now also added at concentrations between 0 mM and 3 mM.

The medium was inoculated and the oxygen saturation kept at over 30% by suitable regulation of the stirrer revolution rate and aeration rate. After consumption of the carbon source, glucose was then metered in from a feed vessel, so that the oxygen concentration did not exceed 30%.

The feed consisted of the aforesaid mineral medium with 2 ml/l of 1 M $MgSO_4$, 2 ml/l of trace element solution, 34 mg/l of thiamine and 660 g/l of glucose (M. I. Viitanen, A. Vasala, P. Neubauer and T. Alatossava, Microbial Cell Factories 2003, 2:2).

Enzyme Preparation

The cell mass obtained was resuspended at 10% in 50 mM Tris-Cl pH 7.0, 1M NaCl and disintegrated in the homogenizer. Next a heat denaturation step was effected in the water-bath at 70° C. for 7.5 mins. The denatured proteins and cell debris were centrifuged off.

The supernatant was concentrated to an activity concentration of 1000 U/ml, brought up to 50% glycerine concentration and stored at −20° C.

For the isolation of the alcohol dehydrogenase, in the process according to the invention the host cells are advantageously homogenized and/or heat denatured in a medium which contains ions which are selected from the group consisting of ions of the elements of the first and second main groups of the periodic system, ammonium ions and iron ions, at a concentration of at least 0.2 M.

The invention also relates to the use of the alcohol dehydrogenase ADH T for the stereoselective production of hydroxy compounds by enzymatic reduction of ketone compounds by means of the alcohol dehydrogenase in a medium which contains ions which are selected from the group consisting of ions of the elements of the first and second main groups of the periodic system, ammonium ions and iron ions, at a concentration of at least 0.2 M.

The invention further relates to a process for the stereoselective production of secondary alcohols, wherein keto compounds are enzymatically reduced by an alcohol dehydrogenase ADH T in a medium which contains ions which are selected from the group consisting of ions of the elements of the first and second main groups of the periodic system, ammonium ions and iron ions, at a concentration of at least 0.2 M.

SEQUENCE LISTING

<160> NUMBER OF SEQ ID NOS: 2

<210> SEQ ID NO 1
<211> LENGTH: 1059

```
<212> TYPE: DNA
<213> ORGANISM: Thermoanaerobacter species

<400> SEQUENCE: 1
atgaaaggtt ttgcaatgct cagtatcggt aaggttggct ggattgaggt agaaaagcct      60
aatccaggac cctttgatgc tatcgtaaga cccctagctg tggccccttg ctcttcggac     120
attcacactg tttttgaagg aggccttggt gaacttcaca acgcagtgct aggtcacgaa     180
gctgtaggtg aagtagtcga agtcggtagt gaagtaaaag actttaaacc tggtgataag     240
gtggtcattc ctgctatcac tcctgattgg agaacgttag atgttcaacg tggttatcat     300
cagcagtccg gaggtatgct tgctggttac aagttcacag cccagaaacc tggtgtgttc     360
gccgagtaca tctacgttaa cgatgcagac atgaatcttg ctcatttacc tgacggcatc     420
tctttagaag cggccgtcat gatcacagat atgatgacta ccggttttca cggagccgaa     480
ctggcagaaa tagaattagg tgcaacagta gcggttttgg gtattggtcc agtaggtctt     540
atggcagtcg ctggtgccaa attgcggggt gctggaagaa ttattgcagt aggcagtaga     600
cctgtttgtg tagatgctgc aaaatactat ggagctactg atattgtaaa ctataaaaat     660
ggtcctatcg acagtcagat tatggattta acgaaaggca aagtgttga tgctgccatc     720 atcgctggag gaaatgttga catcatggct acagcagtta agattgttaa acctggtggc     780
accattgcta atgtaaatta ctttggcgaa ggagatgttt gcctgttcc tcgtcttgaa     840 tggggttgcg gcatggctca taaagctata aaaggcggtt tatgccctgg tggacgtcta     900
agaatggaaa gactgattga ccttgttttt tataagcgtg tcgatccttc caaactcgtc     960
actcatgttt ttcaaggatt tgataatatt gaaaaagctc taatgctgat gaaagataaa    1020
ccaaaggacc taatcaaacc tgttgtaata ttagcataa                           1059

<210> SEQ ID NO 2
<211> LENGTH: 352
<212> TYPE: PRT
<213> ORGANISM: Thermoanaerobacter species

<400> SEQUENCE: 2

Met Lys Gly Phe Ala Met Leu Ser Ile Gly Lys Val Gly Trp Ile Glu
  1               5                  10                  15

Val Glu Lys Pro Asn Pro Gly Pro Phe Asp Ala Ile Val Arg Pro Leu
             20                  25                  30

Ala Val Ala Pro Cys Ser Ser Asp Ile His Thr Val Phe Glu Gly Gly
         35                  40                  45

Leu Gly Glu Leu His Asn Ala Val Leu Gly His Glu Ala Val Gly Glu
     50                  55                  60

Val Val Glu Val Gly Ser Glu Val Lys Asp Phe Lys Pro Gly Asp Lys
 65                  70                  75                  80

Val Val Ile Pro Ala Ile Thr Pro Asp Trp Arg Thr Leu Asp Val Gln
                 85                  90                  95

Arg Gly Tyr His Gln Gln Ser Gly Gly Met Leu Ala Gly Tyr Lys Phe
            100                 105                 110

Thr Ala Gln Lys Pro Gly Val Phe Ala Glu Tyr Ile Tyr Val Asn Asp
        115                 120                 125

Ala Asp Met Asn Leu Ala His Leu Pro Asp Gly Ile Ser Leu Glu Ala
    130                 135                 140

Ala Val Met Ile Thr Asp Met Met Thr Thr Gly Phe His Gly Ala Glu
145                 150                 155                 160

Leu Ala Glu Ile Glu Leu Gly Ala Thr Val Ala Val Leu Gly Ile Gly
```

-continued

```
                    165                 170                 175
Pro Val Gly Leu Met Ala Val Ala Gly Ala Lys Leu Arg Gly Ala Gly
                180                 185                 190

Arg Ile Ile Ala Val Gly Ser Arg Pro Val Cys Val Asp Ala Ala Lys
            195                 200                 205

Tyr Tyr Gly Ala Thr Asp Ile Val Asn Tyr Lys Asn Gly Pro Ile Asp
        210                 215                 220

Ser Gln Ile Met Asp Leu Thr Lys Gly Lys Gly Val Asp Ala Ala Ile
225                 230                 235                 240

Ile Ala Gly Gly Asn Val Asp Ile Met Ala Thr Ala Val Lys Ile Val
                245                 250                 255

Lys Pro Gly Gly Thr Ile Ala Asn Val Asn Tyr Phe Gly Glu Gly Asp
                260                 265                 270

Val Leu Pro Val Pro Arg Leu Glu Trp Gly Cys Gly Met Ala His Lys
            275                 280                 285

Ala Ile Lys Gly Gly Leu Cys Pro Gly Gly Arg Leu Arg Met Glu Arg
        290                 295                 300

Leu Ile Asp Leu Val Phe Tyr Lys Arg Val Asp Pro Ser Lys Leu Val
305                 310                 315                 320

Thr His Val Phe Gln Gly Phe Asp Asn Ile Glu Lys Ala Leu Met Leu
                325                 330                 335

Met Lys Asp Lys Pro Lys Asp Leu Ile Lys Pro Val Val Ile Leu Ala
                340                 345                 350
```

The invention claimed is:

1. An isolated alcohol dehydrogenase comprising the amino acid sequence of SEQ ID NO:2 which is encoded by a DNA molecule comprising the sequence of SEQ ID NO:1 or the DNA sequence which owing to the genetic code is degenerate to the DNA sequence of SEQ ID NO:1.

2. The alcohol dehydrogenase as claimed in claim 1 characterized in that it has the following amino acid sequence

```
                                                    (SEQ ID NO: 2)
Met Lys Gly Phe Ala Met Leu Ser Ile Gly Lys Val Gly Trp Ile Glu
1               5                   10                  15

Val Glu Lys Pro Asn Pro Gly Pro Phe Asp Ala Ile Val Arg Pro Leu
                20                  25                  30

Ala Val Ala Pro Cys Ser Ser Asp Ile His Thr Val Phe Glu Gly Gly
            35                  40                  45

Leu Gly Glu Leu His Asn Ala Val Leu Gly His Glu Ala Val Gly Glu
        50                  55                  60

Val Val Glu Val Gly Ser Glu Val Lys Asp Phe Lys Pro Gly Asp Lys
165                 70                  75                  80

Val Val Ile Pro Ala Ile Thr Pro Asp Trp Arg Thr Leu Asp Val Gln
                85                  90                  95

Arg Gly Tyr His Gln Gln Ser Gly Gly Met Leu Ala Gly Tyr Lys Phe
                100                 105                 110

Thr Ala Gln Lys Pro Gly Val Phe Ala Glu Tyr Ile Tyr Val Asn Asp
            115                 120                 125

Ala Asp Met Asn Leu Ala His Leu Pro Asp Gly Ile Ser Leu Glu Ala
        130                 135                 140

Ala Val Met Ile Thr Asp Met Met Thr Thr Gly Phe His Gly Ala Glu
145                 150                 155                 160

Leu Ala Glu Ile Glu Leu Gly Ala Thr Val Ala Val Leu Gly Ile Gly
                165                 170                 175

Pro Val Gly Leu Met Ala Val Ala Gly Ala Lys Leu Arg Gly Ala Gly
                180                 185                 190
```

-continued

```
Arg Ile Ile Ala Val Gly Ser Arg Pro Val Cys Val Asp Ala Ala Lys
        195                 200                 205

Tyr Tyr Gly Ala Thr Asp Ile Val Asn Tyr Lys Asn Gly Pro Ile Asp
    210                 215                 220

Ser Gln Ile Met Asp Leu Thr Lys Gly Lys Gly Val Asp Ala Ala Ile
225                 230                 235                 240

Ile Ala Gly Gly Asn Val Asp Ile Met Ala Thr Ala Val Lys Ile Val
            245                 250                 255

Lys Pro Gly Gly Thr Ile Ala Asn Val Asn Tyr Phe Gly Glu Gly Asp
            260                 265                 270

Val Leu Pro Val Pro Arg Leu Gln Trp Gly Cys Gly Met Ala His Lys.
        275                 280                 265
```

3. A process for the stereoselective reduction of secondary alcohols, characterized in that keto compounds are enzymatically reduced by an alcohol dehydrogenase as claimed in claim 1 in a medium which contains ions which are selected from the group consisting of ions of the elements of the first and second main groups of the periodic system, ammonium ions and iron ions, in a concentration of at least 0.2 M.

4. The process as claimed in claim 3, characterized in that the keto compound is selected from the group consisting of aliphatic and aromatic ketones, 2- or 3-keto esters and diketones.

5. The process as claimed in claim 3, characterized in that the keto compound is selected from the group consisting of 2-butanone, 2-hexanone, 2-octanone, monochloroacetone, acetaldehyde, 2-methylbutyraldehyde, diacetyl, 2,4-pentanedione, 2,5-hexanedione, ethyl acetoacetate, ethyl 4-chloroacetoacetate, acetophenone, p-chloroacetophenone, 2-acetylpyridine, 3-butyn-2-one, 1,2-cyclohexanedione, pyruvate, 2-oxobutyric acid, 4-chloro-2-butanone, 4-hydroxy-2-butanone, 3-octanone and phenacyl chloride.

6. An isolated alcohol dehydrogenase comprising the amino acid sequence of SEQ ID NO: 2.

7. A process for the stereoselective reduction of secondary alcohols comprising a) enzymatically reducing a keto compound selected from 2-butanone, 2-hexanone, 2-octanone, monochloroacetone, acetaldehyde, 2-methylbutyraldehyde, diacetyl, 2,4-pentanedione, 2,5-hexanedione, ethyl acetoacetate, ethyl 4-chloroacetoacetate, acetophenone, p-chloroacetophenone, 2-acetylpyridine, 3-butyn-2-one, 1,2-cyclohexanedione, pyruvate, 2-oxobutyric acid, 4-chloro-2-butanone, 4-hydroxy-2-butanone, 3-octanone and phenacyl chloride with the alcohol dehydrogenase of claim 6.

* * * * *